United States Patent [19]

Becker

[11] Patent Number: 4,874,614

[45] Date of Patent: Oct. 17, 1989

[54] PHARMACEUTICAL TABLETING METHOD

[75] Inventor: Wallace E. Becker, Raymond, Wis.

[73] Assignee: Abbott Laboratories, Abbott Park, Ill.

[21] Appl. No.: 303,008

[22] Filed: Jan. 30, 1989

Related U.S. Application Data

[63] Continuation of Ser. No. 75,260, Jul. 16, 1987, abandoned, which is a continuation of Ser. No. 715,693, Mar. 25, 1985, abandoned.

[51] Int. Cl.$^4$ .................... A61K 9/20; A61K 9/26; A61K 31/18; A61K 31/71
[52] U.S. Cl. .................... 424/465; 424/488; 424/489; 514/29; 514/601; 514/781
[58] Field of Search ................ 264/109, 123; 424/465, 424/488, 489

[56] References Cited

U.S. PATENT DOCUMENTS

| | | | |
|---|---|---|---|
| 2,099,402 | 11/1937 | Keller | 167/82 |
| 2,798,024 | 7/1957 | Zapapas et al. | 514/29 |
| 2,853,420 | 9/1958 | Lowey | 167/82 |
| 2,866,735 | 12/1958 | Himelick | 514/29 |
| 2,928,770 | 3/1960 | Bardani | 167/82 |
| 2,953,497 | 9/1960 | Press | 167/82 |
| 2,996,431 | 8/1961 | Barry | 167/82 |
| 3,081,233 | 3/1963 | Enz et al. | 514/29 |
| 3,115,441 | 12/1963 | Hermelin | 167/82 |
| 3,119,742 | 1/1964 | Heimlich et al. | 167/82 |
| 3,488,418 | 1/1970 | Holliday et al. | 424/35 |
| 3,860,733 | 1/1975 | Morse et al. | 424/35 |
| 3,865,935 | 2/1975 | Amann | 514/29 |
| 3,883,647 | 5/1975 | Geller | 424/15 |
| 3,891,755 | 6/1975 | Mehta | 514/29 |
| 3,906,086 | 9/1975 | Guy et al. | 424/20 |
| 3,922,338 | 11/1975 | Estevenel et al. | 424/21 |
| 3,927,194 | 12/1975 | Geller | 424/15 |
| 3,954,959 | 5/1976 | Pedersen | 424/21 |
| 3,961,041 | 6/1976 | Nishimura et al. | 424/35 |
| 4,025,613 | 5/1977 | Guy et al. | 424/21 |
| 4,076,804 | 2/1978 | Singiser et al. | 514/29 |
| 4,079,125 | 3/1978 | Sipos | 424/35 |
| 4,173,626 | 11/1979 | Dempski et al. | 424/19 |
| 4,250,166 | 2/1981 | Maekawa | 424/81 |
| 4,259,315 | 3/1981 | Lippmann et al. | 424/37 |
| 4,289,751 | 9/1981 | Windheuser | 514/29 |
| 4,340,582 | 7/1982 | Kriesel et al. | 514/29 |
| 4,370,313 | 1/1983 | Davies | 424/32 |
| 4,415,547 | 11/1983 | Yu et al. | 424/21 |
| 4,432,966 | 2/1984 | Zeitoun et al. | 424/21 |
| 4,434,152 | 2/1984 | Horvath et al. | 424/19 |
| 4,459,295 | 7/1984 | Higuchi et al. | 514/29 |
| 4,461,759 | 7/1984 | Dunn | 424/22 |
| 4,555,399 | 11/1985 | Hsiao | 424/16 |
| 4,599,326 | 7/1986 | Marvola et al. | 514/29 |

FOREIGN PATENT DOCUMENTS 63266 3/1982 European Pat. Off.

*Primary Examiner*—Shep K. Rose
*Attorney, Agent, or Firm*—Steven F. Weinstock; Edward H. Gorman, Jr.

[57] ABSTRACT

A method of preventing the fracture of coated drug granules during the compression of the granules into a commercially acceptable tablet matrix is disclosed. The method involves incorporating into the matrix, along with the granules, from about 10% to about 50% by weight microcrystalline cellulose.

5 Claims, 1 Drawing Sheet

4,874,614

PHARMACEUTICAL TABLETING METHOD

This application is a continuation of application Ser. No 075,260 filed July 16, 1987, now abandoned, which is a continuation of prior application Ser. No. 715,693 filed on Mar. 25, 1985 (now abandoned).

TECHNICAL FIELD

This invention relates to a process for the improved manufacture of pharmaceutical tablet products containing friable coated granules of an active drug ingredient. In particular, it relates to a method for preventing the fracture of such friable granules as they are compressed into a tablet matrix.

Controlled delivery of drugs from pharmaceutical unit dosage forms frequently involves the use of protective coatings to impart acid- or enzyme-resistance, delayed release, and other desirable properties. A preferred method of employing such coatings is to directly coat a granulation of the desired pharmaceutical active ingredient, to produce granules typically having sizes of from about 10 to about 40 mesh. Such granules can be almost entirely active drug, or can be built up from nonpareil seeds, or by other techniques readily familiar to those of skill in the pharmaceutical manufacturing arts. Such granules can then be combined into tablets by conventional compression techniques.

A difficulty is encountered in compressing such coated granules into commercially usable tablet products. Such granules can be formed into relatively soft tablets using low compression forces. However, the compressive forces required to produce a tablet which is sufficiently strong and cohesive to survive the stresses imposed by commercial packaging and distribution inevitably result in fracture of the friable coating on a substantial percentage of the granules, resulting in uncontrolled rather than controlled release of the drug.

It is an object of this invention to provide a method of tableting friable drug granules which avoids the fracture of the coating on the granules during compression into a tablet. This and other objects of the invention will be evident from the following disclosure.

BACKGROUND ART

Derwent abstract 72731A/41 discloses a pharmaceutical tablet formulation containing enteric coated granules and microcrystalline cellulose. However, the tablet formulation also contains a polymer or waxy substance to which a granule-protecting activity is ascribed. The abstract in no way attributes the granule-protective action to the content of microcrystalline cellulose.

DISCLOSURE OF THE INVENTION

This invention provides a method of preventing the fracture of friable coated drug granules during the compression of the drug granules into a tablet matrix having a hardness sufficient to resist an applied fracturing (crushing) pressure of at least about 15 kg./in$^2$, comprising the step of incorporating into the matrix, along with the granules, from about 10% to about 50% microcrystalline cellulose, by weight of the total matrix.

While not intending to be limited by theory, it is believed that the microcrystalline cellulose imparts a resilient yet rigidifying structure to the tablet matrix which is surprisingly accommodative of compressive loads. In fact, this invention provides for the manufacture of tablets of extraordinary hardness from friable coated granules with minimal fracturing of the granules.

The coated drug granules used in this method can comprise substantially any active ingredient which is commonly granulated for use in pharmaceutical tablet products. Such drugs are well known to those of ordinary skill in the pharmaceutical manufacturing arts. The granules can be made using a single drug or a mixture of drugs, or a mixture of different granules, each containing one or more drugs, can be used. The coating can be an enteric coating, an acid-resistant coating, a microporous coating, or other coating intended to control the release rate or dissolution rate of the drug granule. Among the materials useful for this purpose are acrylic polymers and copolymers, ethylcellulose, hydroxypropylcellulose, hydroxypropylmethylcellulose, polyvinyl acetate, polyvinyl acetate phthalate, cellulose acetate phthalate, hydroxypropylmethylcellulose phthalate, zein, shellac, acacia, nylon, sugar, anionic acrylic resins, and the like.

The microcrystalline cellulose used in the practice of this invention is an article of commerce, available from a variety of sources, and is a National Formulary material. Its manufacture is described by Battista, Ind. Eng. Chem., 42, 502 (1950) and U.S. Pat. Nos. 2,978,446 and 3,141,875. It is a nonfibrous powder having the particulate form of rigid rods and a bulk density of 18 to 19 pounds per cubic foot. It is practically insoluble in water, but is dispersible therein.

Additional tableting aids, excipients, binders, etc., well known to the pharmaceutical arts can also be employed at minor levels (generally less than 10%, preferably less than 2%) in the practice of this invention. Such inert additives include a variety of stearates, tableting aids, starches, gums, waxes, silicates, polymers and the like.

If desired, uncoated granules of drug can also be included in the tablet matrix. Just as the coated granules in a given tablet can be made from a single drug or a number of drugs, the uncoated granules optionally incorporated in the tablet matrix can be the same drug or drugs used in the coated granules, or they may be a different drug or mixture of drugs, as dictated by the desires of the formulator.

The following Examples illustrate the practice of this invention, without intending to be limitative thereof.

EXAMPLE 1

Tablets for the combined administration of enteric-coated granules of erythromycin in conjunction with an uncoated sulfamethoxazole granulation are prepared as follows: 500 grams of sulfamethoxazole and 10 grams of a conventional starch derivative are charged into a mass mixer. Ten grams of cornstarch are added along with sufficient water to make a starch paste. This starch paste is used to make a standard granulation.

Separately, 275 grams of erythromycin and 10 grams of conventional cellulosic binder are charged into a mass mixer. A solution of 10 grams povidone in water is added, and the mixture is granulated. The granulation is dried and sized in similar fashion to the sulfamethoxazole granulation, to yield particles of from 10 to 40 mesh. Oversize and undersize particles are recycled.

Separately, 80 grams of an enteric cellulose phthalate polymer, and 8 grams of an alkyl citrate plasticizer are dispersed in a sufficient quantity of USP acetone and alcohol to make a solution. 0.3 grams of blue dye lake are added, and the dispersion is stirred to mix. The erythromycin granulation is coated with this solution in a particle coater and the resultant coated particles are sized. Separately, a portion of the sulfamethoxazole granulation is charged into a blender. The dried erythromycin coated particles, sized to 10 to 40 mesh, are added, as well as 200 grams of microcrystalline cellulose, NF; and 4 grams of conventional lubricants and glidants. The remainder of the sulfamethoxazole granulation is added and the mixture is blended. This blended material is compressed into tablets having a weight per 10 tablets of approximately 12 grams.

EXAMPLE 2

Figure 1:
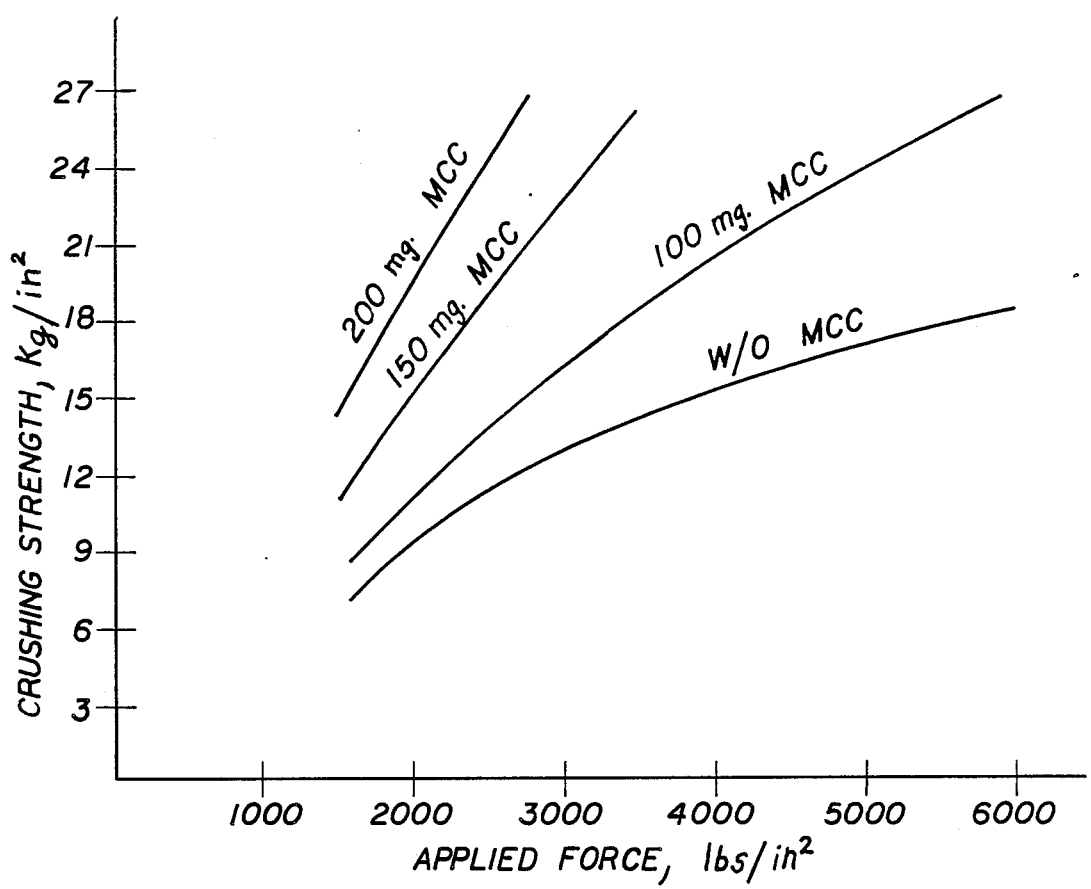
FIG. 1 is a graph plotting applied tableting force (lbs/in$^2$) in the tableting process of this invention versus crushing strength of the resulting tablets for four different levels of microcrystalline cellulose (MCC) content.

Erythromycin/sulfamethoxazole tablet granulations were prepared in a manner similar to that of Example 1, but containing varying quantities of microcrystalline cellulose. Tablets were pressed in a conventional tablet press at applied forces of from 1500 pounds per square inch to 6000 pounds per square inch, and the hardness of the resulting tablets was measured using a modified Strong-Cobb hardness tester. Hardness is measured in kilograms per square inch applied fracturing force at the point of fracture of the tablet, averaged over ten tablets. In general, large tablets having a hardness sufficient to resist applied fracturing forces greater than 15 $kg/in^2$ will readily withstand the stresses imposed by conventional commercial packaging and distribution, tablets having a hardness greater than 20 $kg/in^2$ are considered very hard, and tablets having a hardness greater than 25 $kg/in^2$ are considered extremely hard. The results of tests on tablets made in accordance with this invention are plotted in FIG. 1. While hardness of the tablets varied proportionally with applied tableting force, higher levels of microcrystalline cellulose provided a greater tablet hardness for a given applied tableting force.

EXAMPLE 3

Figure 2:
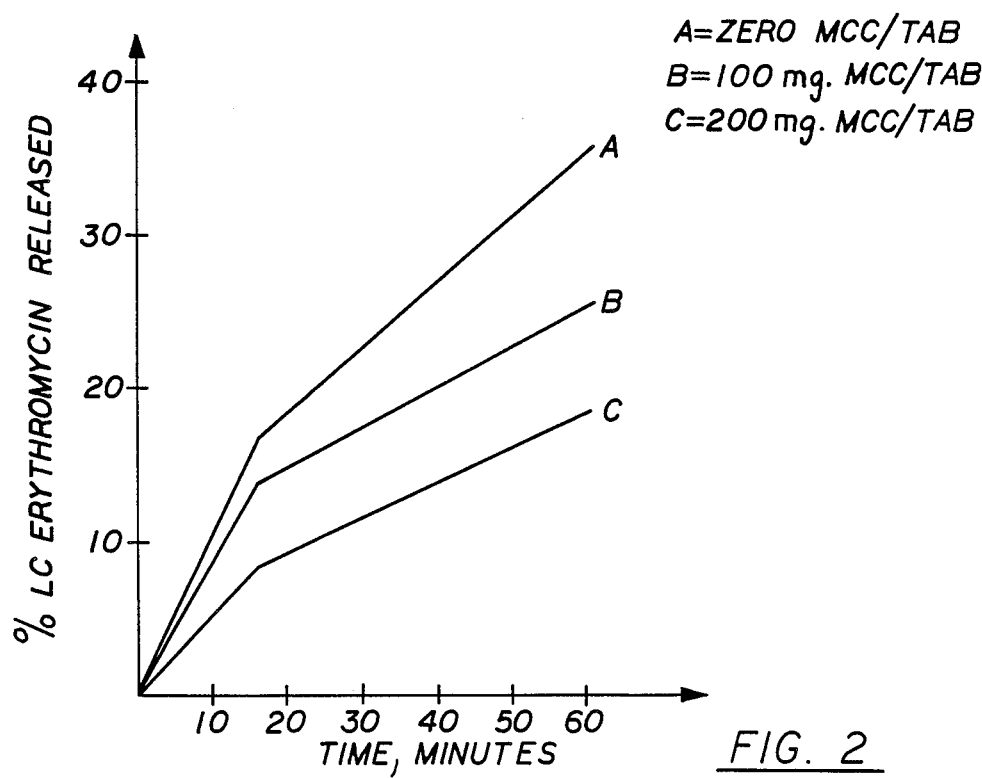
FIG. 2 is a graph plotting time versus % of the erythromycin content released from tablets in an acid medium for three different levels of microcrystalline cellulose (MCC).

Tablets prepared according to Examples 1 and 2 using a compression force of 6000 pounds per square inch were placed in acid medium (pH 1.2), and the amount of erythromycin released was measured as a function of time and calculated as a percentage of the label-claim (LC) content of the drug. The coating on the erythromycin granules was an enteric coating, i.e., selected to be acid resistant. Thus, the erythromycin release as a junction of time was a direct indicator of the proportion of coated granules fractured during the tableting process. The results are depicted in FIG. 2 of the drawings. It can be seen that increasing levels of microcrystalline cellulose provide increased protection against fracture of the enteric coating, even when the tablets were compressed at a tableting force of 6000 psi. At 200 milligrams of microcrystalline cellulose per tablet, the tablet formulation exhibited roughly half the premature (uncontrolled) release of erythromycin exhibited by the tablet formulation containing no microcrystalline cellulose.

Further tests were performed on tablets containing 200 mg. microcrystalline cellulose per tablet to quantify this phenomenon. In addition to measuring erythromycin release, disintegration times for the tablets were determined by performing conventional USP disintegration test procedures, as described in USP XX, Mack Publishing Co., Easton, PA, 1980, pp. 958–960, the disclosures of which are hereby incorporated herein by reference. The USP Disintegration Apparatus (Stoll-Gershberg apparatus) without discs was employed, using distilled water as the aqueous medium. Disintegration time was identified as the time to complete passage of the tablet (as disintegrated) through a 10-mesh screen. Results are provided in the following table.

| Compression Force, $lbs/in^2$ | 1500 | 3000 | 4500 | 6000 |
|---|---|---|---|---|
| Erythromycin Released in Acid Media, 15 min., % LC | 6.6 | 7.1 | 6.6 | 5.4 |
| Erythromycin Released in Acid Media, 60 min. % LC | 16.3 | 15.6 | 15.7 | 13.3 |
| Tablet Disintegration Time in distilled water min. | 1.0 | 1.6 | 4.4 | 8.5 |

What is claimed is:

1. In an improved method of making a pharmaceutical tablet comprised of a tablet matrix of friable enteric or controlled release coated fracturable granules and the tablet having a hardness sufficient to resist an applied fracturing pressure of at least $15kg/in^2$, the improvement comprising: incorporating into the matrix prior to applying at least said fracturing pressure, microcrystalline cellulose in the amount of from about 10% to about 50%, by weight of the total matrix.

2. A method according to claim 1, wherein the granules have an enteric coating.

3. A method according to claim 2 wherein the matrix further comprises noncoated drug granules.

4. A method according to claim 3 wherein the noncoated granules comprise the same drug as the friable enteric coated granules.

5. A method according to claim 3 wherein the noncoated drug granules contain a drug different from the drug in the friable enteric coated granules.

* * * * *

UNITED STATES PATENT AND TRADEMARK OFFICE
CERTIFICATE OF CORRECTION

PATENT NO. : 4,874,614

DATED : October 17, 1989

INVENTOR(S) : Becker, Wallace E.

It is certified that error appears in the above-identified patent and that said Letters Patent is hereby corrected as shown below:

Column 3, line 57: Replace "junction" with --function--

Signed and Sealed this

First Day of January, 1991

Attest:

HARRY F. MANBECK, JR.

*Attesting Officer*      *Commissioner of Patents and Trademarks*